(12) United States Patent
McAlister

(10) Patent No.: US 9,127,244 B2
(45) Date of Patent: Sep. 8, 2015

(54) DIGESTER ASSEMBLY FOR PROVIDING RENEWABLE RESOURCES AND ASSOCIATED SYSTEMS, APPARATUSES, AND METHODS

(71) Applicant: McAlister Technologies, LLC., Phoenix, AZ (US)

(72) Inventor: Roy Edward McAlister, Phoenix, AZ (US)

(73) Assignee: McAlister Technologies, LLC, Phoenix, AZ (US)

( * ) Notice: Subject to any disclaimer, the term of this patent is extended or adjusted under 35 U.S.C. 154(b) by 0 days.

(21) Appl. No.: 13/828,549

(22) Filed: Mar. 14, 2013

(65) Prior Publication Data
US 2014/0273196 A1 Sep. 18, 2014

(51) Int. Cl.
*C12M 3/00* (2006.01)
*C02F 11/00* (2006.01)
*C12M 1/107* (2006.01)

(52) U.S. Cl.
CPC .............. *C12M 21/04* (2013.01); *Y02E 50/343* (2013.01); *Y10T 29/49826* (2015.01)

(58) Field of Classification Search
CPC ...... C12M 23/26; C12M 23/14; C12M 23/04; C12M 23/06; C02F 11/04; C02F 11/02
See application file for complete search history.

(56) References Cited

U.S. PATENT DOCUMENTS

| | | | |
|---|---|---|---|
| 1,771,091 A | 7/1930 | Lawaczeck | |
| 3,410,770 A | 11/1968 | Buechler | |
| 3,812,026 A | 5/1974 | Bertrand et al. | |
| 3,855,386 A | 12/1974 | Moore | |
| 4,019,868 A | 4/1977 | Sebacher et al. | |
| 4,053,576 A | 10/1977 | Fletcher | |
| 4,142,950 A | 3/1979 | Creamer et al. | |

(Continued)

FOREIGN PATENT DOCUMENTS

| | | |
|---|---|---|
| AT | 346826 T | 12/2006 |
| AU | 2122100 A | 8/2001 |

(Continued)

OTHER PUBLICATIONS

"Electrifying New Way to Clean Dirty Water." University of Utah, Published: Jan. 5, 2011. Accessed: Jun. 1, 2011. <http://www.unews.utah.edu/old/p/010511-1.html>.

(Continued)

*Primary Examiner* — Nathan Bowers
(74) *Attorney, Agent, or Firm* — Perkins Coie LLP

(57) ABSTRACT

A renewable energy system includes a digester assembly having an outer tube with an input region and a digestion region. The input region extends above grade and is configured to receive liquid waste. At least a portion of the digestion region is positioned below grade and configured to receive the liquid waste and to anaerobically digest the liquid waste with microorganisms to supply renewable byproducts, such as methane, hydrogen, carbon dioxide, and/or carbon dioxide-rich water. The digester assembly can include two or more deformable tubes that are configured to move liquid through the outer tube by alternatingly compressing one another. In one embodiment, the deformable tubes are configured to replenish waste liquid and to deliver liquid byproducts. In another embodiment, the deformable tubes are configured to exhaust air, such as for delivery of gas byproducts and fostering an anaerobic environment.

13 Claims, 4 Drawing Sheets

(56) References Cited

U.S. PATENT DOCUMENTS

| | | | |
|---|---|---|---|
| 4,169,035 A | 9/1979 | Stummer et al. | |
| 4,200,505 A | 4/1980 | Day et al. | |
| 4,243,503 A | 1/1981 | Lieb et al. | |
| 4,282,187 A | 8/1981 | Corbett et al. | |
| 4,339,547 A | 7/1982 | Corbett et al. | |
| 4,341,608 A | 7/1982 | St. John | |
| 4,343,690 A | 8/1982 | de Nora | |
| 4,343,770 A | 8/1982 | Simons | |
| 4,354,905 A | 10/1982 | Yoshida et al. | |
| 4,374,014 A | 2/1983 | Smith et al. | |
| 4,377,455 A | 3/1983 | Kadija et al. | |
| 4,391,793 A | 7/1983 | Boese | |
| 4,395,316 A | 7/1983 | St. John | |
| 4,417,861 A * | 11/1983 | Tolbert | 417/315 |
| 4,468,311 A | 8/1984 | de Nora et al. | |
| 4,497,112 A | 2/1985 | Dang et al. | |
| 4,519,342 A | 5/1985 | Yoon | |
| 4,528,270 A | 7/1985 | Matsunaga | |
| 4,548,693 A | 10/1985 | Kadija et al. | |
| 4,568,522 A | 2/1986 | Corbett | |
| 4,574,037 A | 3/1986 | Samejima et al. | |
| 4,645,594 A * | 2/1987 | Lingo, Sr. | 435/290.2 |
| 4,896,507 A | 1/1990 | Hosford | |
| 5,015,342 A | 5/1991 | Ginatta et al. | |
| 5,360,522 A | 11/1994 | Kuroda et al. | |
| 5,589,052 A | 12/1996 | Shimamune et al. | |
| 5,660,698 A | 8/1997 | Scannell et al. | |
| 5,711,865 A | 1/1998 | Caesar | |
| 5,779,866 A | 7/1998 | Tarancon | |
| 5,882,382 A | 3/1999 | Hachisuka et al. | |
| 5,904,821 A | 5/1999 | Blank et al. | |
| 6,090,266 A | 7/2000 | Roychowdhury | |
| 6,238,546 B1 | 5/2001 | Knieper et al. | |
| 6,328,863 B1 | 12/2001 | Wilhelm et al. | |
| 6,395,252 B1 | 5/2002 | Getty et al. | |
| 6,446,597 B1 | 9/2002 | McAlister | |
| 6,464,755 B2 | 10/2002 | Nakanishi et al. | |
| 6,471,873 B1 | 10/2002 | Greenberg et al. | |
| 6,495,023 B1 | 12/2002 | Zeikus et al. | |
| 6,525,263 B2 | 2/2003 | Muller | |
| 6,645,442 B2 | 11/2003 | Kaneko et al. | |
| 6,698,389 B2 | 3/2004 | Andrews et al. | |
| 6,780,306 B2 | 8/2004 | Schlager et al. | |
| 6,802,956 B2 | 10/2004 | Orlebeke | |
| 6,984,305 B2 | 1/2006 | McAlister | |
| 7,097,748 B2 | 8/2006 | Duffy et al. | |
| 7,138,046 B2 | 11/2006 | Roychowdhury | |
| 7,141,147 B2 | 11/2006 | Shimamune | |
| 7,224,080 B2 | 5/2007 | Smedstad | |
| 7,250,288 B2 | 7/2007 | Zeikus et al. | |
| 7,318,885 B2 | 1/2008 | Omasa | |
| 7,351,316 B2 | 4/2008 | Yoshida et al. | |
| 7,448,214 B2 | 11/2008 | Monostory et al. | |
| 7,491,453 B2 | 2/2009 | Logan et al. | |
| 7,507,490 B2 | 3/2009 | Ohtani et al. | |
| 7,510,633 B2 | 3/2009 | Shimko et al. | |
| 7,510,640 B2 | 3/2009 | Gibson et al. | |
| 7,560,274 B1 * | 7/2009 | Fuller et al. | 435/297.1 |
| 7,563,371 B2 | 7/2009 | McCune-Sanders et al. | |
| 7,645,930 B2 | 1/2010 | Kelly et al. | |
| 7,645,931 B2 | 1/2010 | Gibson et al. | |
| 7,651,602 B2 | 1/2010 | Helmke et al. | |
| 7,674,538 B2 | 3/2010 | Grieve et al. | |
| 7,709,113 B2 | 5/2010 | Logan et al. | |
| 7,744,675 B2 | 6/2010 | Saukaitis et al. | |
| 7,762,495 B2 | 7/2010 | Miller | |
| 7,834,223 B2 | 11/2010 | Atkins et al. | |
| 7,887,679 B2 | 2/2011 | Kitaori et al. | |
| 7,897,429 B2 | 3/2011 | Simmons et al. | |
| 7,922,795 B2 | 4/2011 | Striemer et al. | |
| 7,922,878 B2 | 4/2011 | Logan | |
| 8,075,748 B2 | 12/2011 | McAlister | |
| 8,075,749 B2 | 12/2011 | McAlister | |
| 8,075,750 B2 | 12/2011 | McAlister | |
| 8,172,990 B2 | 5/2012 | McAlister | |
| 2002/0108866 A1 | 8/2002 | Bonilla Griz | |
| 2002/0110522 A1 | 8/2002 | Chin | |
| 2003/0012985 A1 | 1/2003 | McAlister | |
| 2003/0062270 A1 | 4/2003 | McAlister | |
| 2003/0129469 A1 | 7/2003 | Sun et al. | |
| 2003/0210985 A1 * | 11/2003 | Feygin et al. | 417/46 |
| 2005/0183962 A1 | 8/2005 | Oakes | |
| 2006/0147763 A1 | 7/2006 | Angenent et al. | |
| 2006/0272955 A1 | 12/2006 | Felder et al. | |
| 2006/0272956 A1 | 12/2006 | Felder et al. | |
| 2007/0056842 A1 | 3/2007 | Roychowdhury | |
| 2007/0170113 A1 * | 7/2007 | Lenger et al. | 210/608 |
| 2007/0251830 A1 | 11/2007 | Conrad | |
| 2007/0259216 A1 | 11/2007 | Logan | |
| 2007/0259217 A1 | 11/2007 | Logan | |
| 2007/0274905 A1 | 11/2007 | Wynn | |
| 2008/0047502 A1 | 2/2008 | Morse | |
| 2008/0152967 A1 | 6/2008 | Roychowdhury | |
| 2008/0245660 A1 | 10/2008 | Little et al. | |
| 2008/0245672 A1 | 10/2008 | Little et al. | |
| 2008/0248350 A1 | 10/2008 | Little et al. | |
| 2008/0292912 A1 | 11/2008 | Logan et al. | |
| 2008/0311022 A1 | 12/2008 | Carrington et al. | |
| 2009/0007484 A1 | 1/2009 | Smith | |
| 2009/0048354 A1 | 2/2009 | Bell et al. | |
| 2009/0139856 A1 | 6/2009 | Chiarini, Jr. | |
| 2009/0260363 A1 | 10/2009 | Moriarty | |
| 2010/0003184 A1 | 1/2010 | Nakamura | |
| 2010/0107994 A1 | 5/2010 | Moriarty et al. | |
| 2010/0119920 A1 | 5/2010 | Logan et al. | |
| 2010/0151279 A1 | 6/2010 | Logan et al. | |
| 2010/0213050 A1 | 8/2010 | McAlister | |
| 2010/0284749 A1 | 11/2010 | Capron | |
| 2011/0083971 A1 | 4/2011 | Roychowdhury | |
| 2011/0253526 A1 | 10/2011 | McAlister | |
| 2011/0257275 A1 | 10/2011 | McAlister | |
| 2011/0318778 A1 | 12/2011 | Petersen et al. | |
| 2013/0011896 A1 * | 1/2013 | Strehler | 435/167 |

FOREIGN PATENT DOCUMENTS

| | | |
|---|---|---|
| AU | 2005248951 | 2/2006 |
| AU | 2007248040 A1 | 11/2007 |
| BR | 017078 | 11/2002 |
| CA | 2154465 A1 | 8/1994 |
| CA | 2399400 A1 | 8/2001 |
| CA | 2650818 A1 | 11/2007 |
| CN | 1243669 A | 2/2000 |
| CN | 1437564 A | 8/2003 |
| CN | 201003075 Y | 1/2008 |
| CN | 101485029 A | 7/2009 |
| DE | 60032179 T2 | 9/2007 |
| EP | 1263686 A1 | 12/2002 |
| EP | 1939968 A1 | 7/2008 |
| EP | 2025033 A2 | 2/2009 |
| ES | 2275490 T3 | 6/2007 |
| FR | 2286891 A1 | 4/1976 |
| JP | 2003521258 T | 7/2003 |
| JP | 2004307878 A | 11/2004 |
| KR | 10-0808736 B1 | 2/2008 |
| KR | 101218952 | 1/2013 |
| MX | 02007361 | 9/2004 |
| WO | WO-0156938 A1 | 8/2001 |
| WO | WO-03042430 A2 | 5/2003 |
| WO | WO-2004094698 A1 | 11/2004 |
| WO | WO-2006010149 A2 | 1/2006 |
| WO | WO-2006130557 A2 | 12/2006 |
| WO | WO-2007039661 A1 | 4/2007 |
| WO | WO-2007131022 A2 | 11/2007 |
| WO | WO-2007131029 A2 | 11/2007 |
| WO | WO-2008036347 A2 | 3/2008 |
| WO | WO-2008/124538 A1 | 10/2008 |
| WO | WO-2009003006 A1 | 12/2008 |
| WO | WO-2010013244 A2 | 2/2010 |

OTHER PUBLICATIONS

"INOTEC—Cutting-Edge Wastewater Treatment." Accessed: Jan. 31, 2011. <http://www.inotec.us/>. pp. 1-3.

(56) References Cited

OTHER PUBLICATIONS

"New Electrolytic Cells to Play a Role in Tomorrow's Local Energy Supply." Science Blog. Published: Apr. 27, 2010. Accessed: Jun. 1, 2011. <http://scienceblog.com/33189/new-electrolytic-cells-to-play-a-role-in-tomorrows-local-energy-supply/>. pp. 1-5.
"U of U Scientists Electrify Microbes to Clean Dirty Water." Water and Wastewater.Com, Water Treatment Equipment Homepage. Published: Jan. 18, 2011. Accessed: May 27, 2011. <http://www.waterandwastewater.com/www_services/news_center/publish/industry_news/U_of_U_Scientists_Electrify_Microbes_to_Clean_Dirty_Water_printer.shtml>. pp. 1-2.
"Utah Microbubbles Clean Dirty Soil in China." University of Utah, Published: Oct. 13, 2010. Accessed: May 27, 2011. <http://unews.utah.edu/old/p/101110-1.html>. pp. 1-2.
Bioremediation and Bioprocess Consulting, LLC. "Biocapsules Time-Release of Microbes and/or Nutrients." Inotec.com; Published: 2003. Accessed: Jan. 31, 2011. p. 1.
Chen et al. "Parylene-Encapsulated Copolymeric Membranes as Localized and Sustained Drug Delivery Platforms." Annals of Biomedical Engineering, vol. 37, Issue 10 (2009). pp. 2003-2017.
McConnell et al. "A Hybrid Solar Concentrator for the Electrolytic Production of Hydrogen." U.S.Department of Energy, National Renewable Energy Laboratory, Howard University, Published: Dec. 12, 2005. Web. Accessed: Jun. 8, 2011. <http://www1.eere.energy.gov/solar/pdfs/mcconnell.pdf>. pp. 1-23.
Examiner's Report issued for Canadian National Phase Application No. 2,752,698 based on PCT/US10/24499, Date of Filing of Application: Feb. 17, 2010, Date of Mailing: Jul. 31, 2012, 3 pages.
Office Action issued for Japanese National Phase Application No. 2011-551197 based on PCT/USUS10/24497, Date of Filing of Application: Feb. 17, 2010, Date of Mailing: Aug. 27, 2012, 3 pages.
Office Action issued for Japanese National Phase Application No. 2011-551196 based on PCT/USUS10/24496, Date of Filing of Application: Feb. 17, 2010, Date of Mailing: Aug. 27, 2012, 4 pages.
Office Action issued for Japanese National Phase Application No. 2011-551198 based on PCT/USUS10/24498, Date of Filing of Application: Feb. 17, 2010, Date of Mailing: Aug. 27, 2012, 2 pages.
European Search Report for EP 12167100.2 filed on Feb. 17, 2010 based on PCT/US2010/096504; Date of Mailing: Oct. 31, 2012, 8 pages.
International Search Report and Written Opinion for Application No. PCT/US2010/002259; Applicant: McAlister Technologies, LLC.; Date of Mailing: May 2, 2011; 9 pages.
International Search Report and Written Opinion for Application No. PCT/US2010/024498; Applicant: McAlister Technologies, LLC.; Date of Mailing: Apr. 23, 2010; 7 pages.
International Search Report and Written Opinion for Application No. PCT/US2010/024816; Applicant: McAlister Technologies, LLC.; Date of Mailing: Feb. 24, 2012; 15 pages.
International Search Report and Written Opinion for Application No. PCT/US2010/24497; Applicant: McAlister Technologies, LLC.; Date of Mailing: Apr. 12, 2010; pp. 1-14.
International Search Report and Written Opinion for Application No. PCT/US2010/24499; Applicant: McAlister Technologies, LLC.; Date of Mailing: Apr. 21, 2010; 9 pages.
Rozendal, R. A., et al., "Principle and perspectives of hydrogen production through biocatalyzed electrolysis," International Journal of Hydrogen Energy, Elsevier Science Publishers B.V., Barking, GB, vol. 31, No. 12, Sep. 1, 2006, pp. 1632-1640.
Supplementary European Search Report for EP 10744269.1 filed on Feb. 17, 2010 based on PCT/US2010/024497 Date of Mailing: Oct. 31, 2012, 6 pages.
Supplementary European Search Report for EP 10744271.7 filed on Feb. 17, 2010 based on PCT/US2010/024499; Date of Mailing: Oct. 31, 2012, 22 pages.
Yagi et al., "A New Method for Hydrogenase Based on an Enzymic Electrode Reaction," J. Biochem., 78, 1975, pp. 443-454.
Yagi, "Separation of hydrogenase-catalyzed hydrogen-evolution system from electron-donating system by means of enzymic electric cell technique," Proc, Natl. Acad. Sci. USA, vol. 73, No. m9, Sep. 1976, pp. 2947-2949.
International Search Report and Written Opinion for International Application No. PCT/US14/26160; Applicant McAlister Technologies, LLC.; Date of Mailing Sep. 4, 2014; pp. 11.

\* cited by examiner

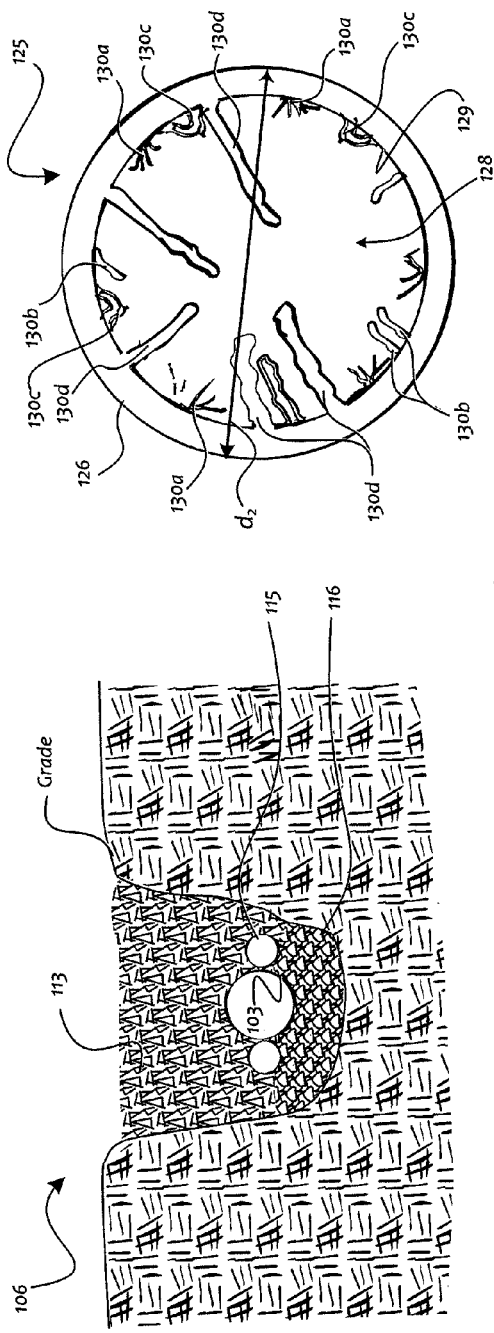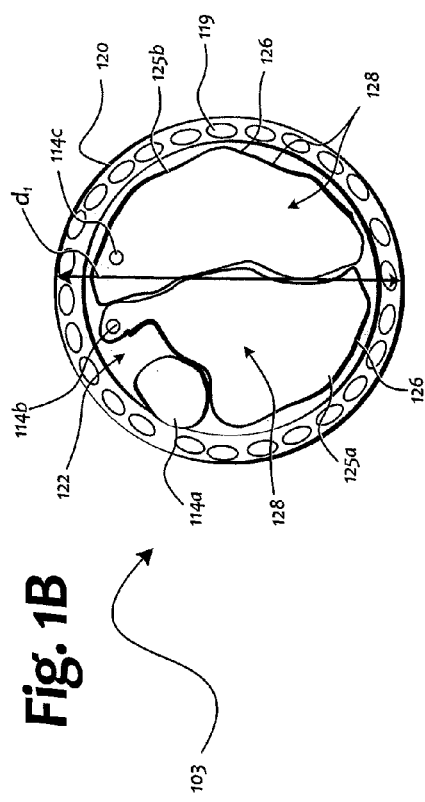
Fig. 1B
Fig. 1C
Fig. 1D

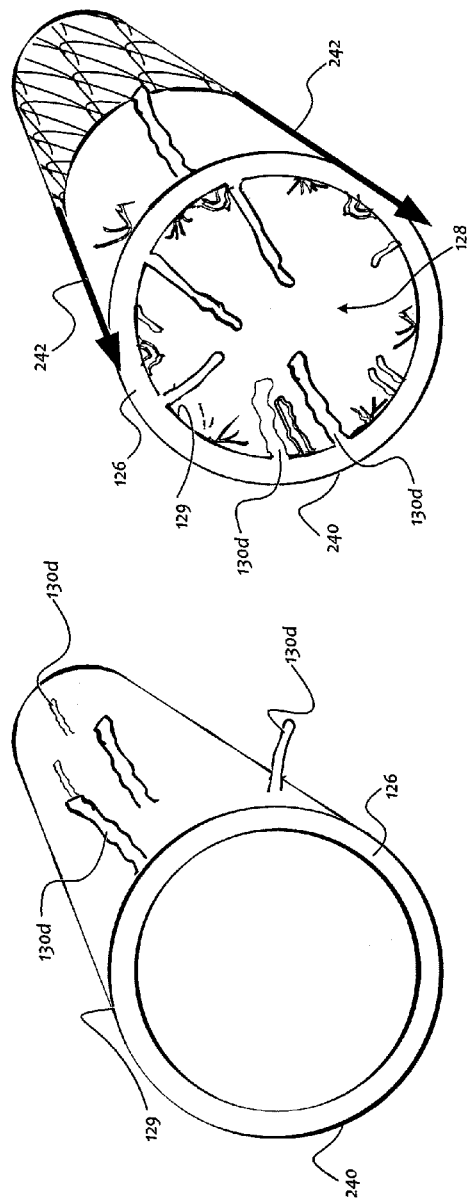
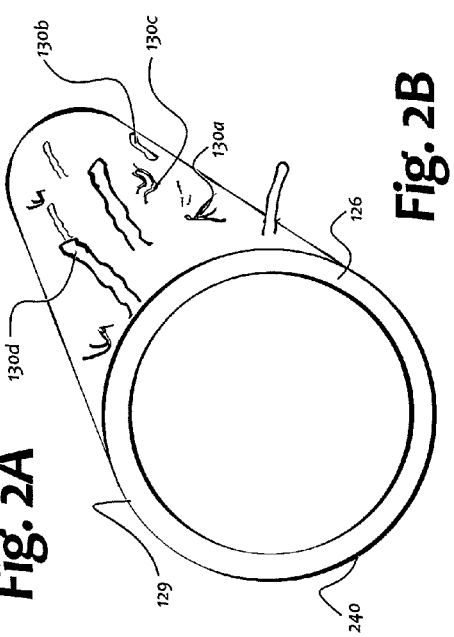

DIGESTER ASSEMBLY FOR PROVIDING RENEWABLE RESOURCES AND ASSOCIATED SYSTEMS, APPARATUSES, AND METHODS

TECHNICAL FIELD

The following disclosure relates generally to systems, apparatuses, and methods for converting waste materials into renewable resources, such as renewable fuels and food sources.

BACKGROUND

Animal life is supported by chemical processes that occur in the intestinal system. These processes can be supported in part by microorganisms that anaerobically digest food into various byproducts. The circulatory system can then deliver these byproducts to tissue cells, and the tissue cell can in turn metabolize the byproducts.

BRIEF DESCRIPTION OF THE DRAWINGS

Many aspects of the disclosure can be better understood with reference to the following drawings. The dimensions, angles, and other specifications shown in the drawings are merely illustrative of particular embodiments of the disclosure. Other embodiments can have other dimensions, angles, and specifications without departing from the spirit or scope of the disclosure.

FIGS. 1A-1D are various diagrams illustrating a renewable energy system including a digester configured in accordance with an embodiment of the present technology.

FIGS. 2A-2C are isometric diagrams that show various stages in a method for manufacturing deformable tubes of the digester of FIGS. 1A-1D in accordance with an embodiment of the present technology.

DETAILED DESCRIPTION

The following disclosure describes various embodiments of systems, apparatuses, and methods using anaerobic microorganisms to produce renewable fuels from waste sources, such as animal wastes and/or soil wastes. Certain details are set forth in the following description and in FIGS. 1A-3 to provide a thorough understanding of various embodiments of the present technology. Those of ordinary skill in the relevant art will appreciate, however, that the present technology can have additional embodiments that may be practiced without several of the details described below. In addition, some well-known aspects of microorganisms and their digestive processes have not been shown or described in detail below to avoid unnecessarily obscuring the description of the various embodiments of the present technology.

Figure 1A:
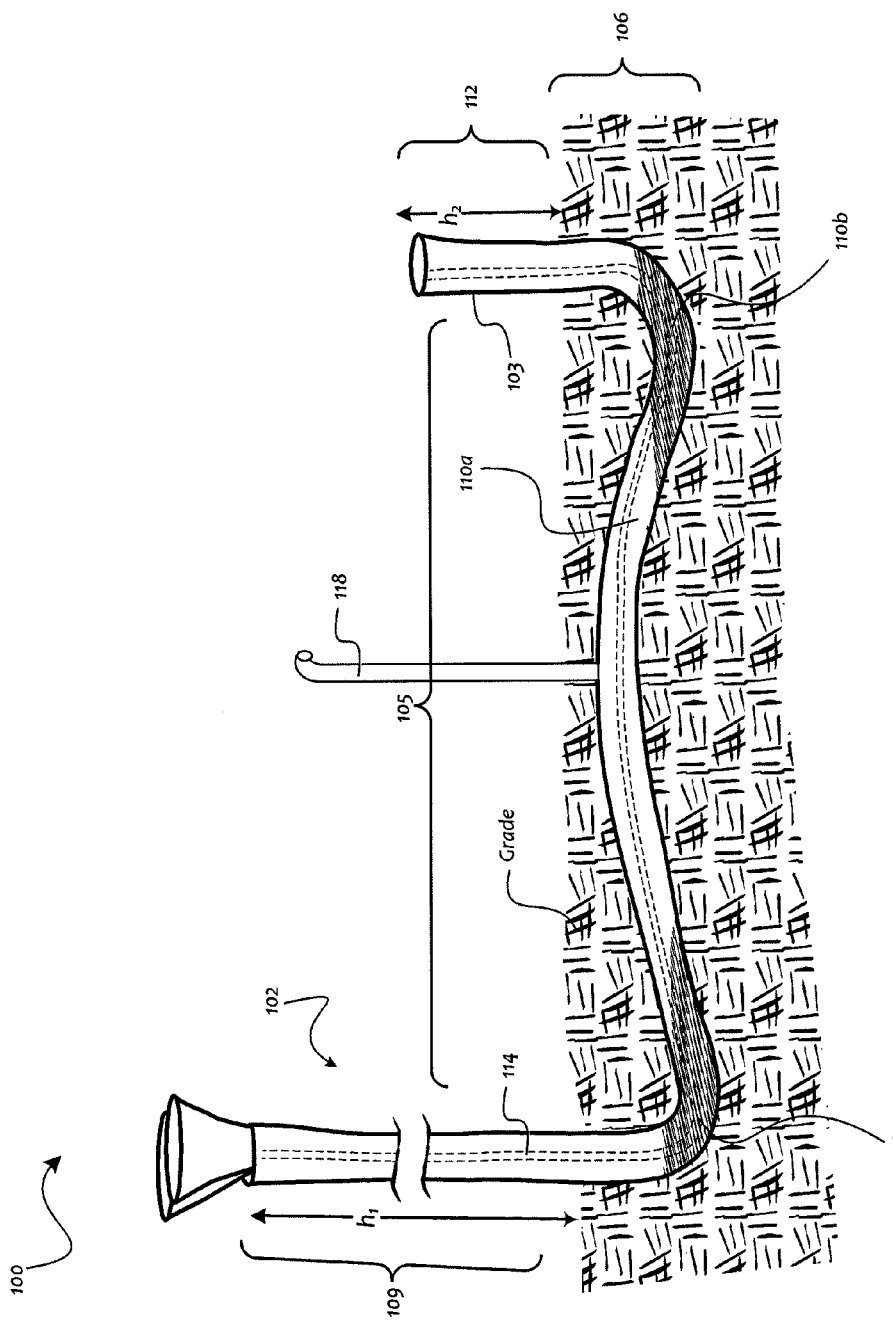

FIG. 1A is a diagram illustrating a renewable energy system 100 configured in accordance with an embodiment of the present technology. The system 100 includes a digester assembly 102 ("digester 102") having an outer tube 103. The outer tube 103 is positioned to form an input region 109, an output region 112, and a digestion region 105 in a trench 106 between the input region 109 and the output region 112. The input region 109 extends above grade by a height $h_1$, and the output region 112 extends above grade by a second height $h_2$ that is less than the first height $h_1$. In one embodiment, the top of the input region 109 can be located on a hill above the output region 112.

In operation, a person or operator can pour a liquid waste 108 (e.g., from a container, vessel, etc.) into the input region 109 of the digester 102. Alternatively, in some embodiments a mechanical pump can supply the liquid waste 108 to the digester 102. The liquid waste 108 can include liquid phase and solid phase components. For example, the liquid waste 108 can include liquid and/or solid phase components of animal waste, plant waste, and/or soil waste. As described in greater detail below, the digestion region 105 receives the liquid waste 108 and utilizes the anaerobic digestion of microorganisms to supply renewable byproducts 110 (identified individually as gas byproducts 110a and liquid byproducts 110b; only liquid byproducts 110b are shown in FIG. 1A). In one aspect of this embodiment, the gas byproducts 110a (e.g., methane, hydrogen, and/or carbon dioxide) flow in one or more gas collection conduits 114 toward the output region 112 and optionally toward the input region 109. In some embodiments, the digester 102 can include a "blowhole" tube that extends through grade to collect the gas byproducts 110a. In another aspect of this embodiment, the output region 112 can deliver the liquid byproducts 110b toward a greenhouse, a crop field, or other suitable area. The liquid byproducts 110b can include, for example, carbon dioxide-rich water and other nutrients that are suitable in hydroponic systems for growing duckweed, algae, or various hydroponic or aeroponic crops.

FIG. 1B is a cross-sectional view of the trench 106. The trench 106 at least partially contains insulating material 113, heat-transfer elements 115, drainage 116, and the outer tube 103. The insulating material 113 can include a variety of thermally insulative materials, such as a polymer sheet and/or on-site materials (e.g., manure, soil, shredded paper, straw, etc.). The heat-transfer elements 115 can include, for example, plastic piping that contains a heat-transfer fluid, such as solar hot water. The drainage 116 can include plastic piping, gravel, and/or other suitable features to draw away surface water from the trench 106. In some embodiments, the system 100 can omit one or more of the insulating material 113, the heat-transfer elements 115, and/or the drainage 116. For example, in one embodiment an inventory of the liquid waste 108 and/or the liquid byproducts 110b (FIG. 1A) can maintain temperature in the outer tube 103.

In operation, the trench 106 provides a suitable temperature for sustaining microorganisms in the digestion region 105 (FIG. 1A). In one aspect of this embodiment, the byproducts 110 can at least partially dictate the operating temperatures. For example, the trench 106 can optimize methane production by being configured to minimize a thermal gradient between the digestion region 105 and the above-grade environment. In another aspect of this embodiment, the microorganisms can at least partially dictate the operating temperatures. For example, some anaerobic microorganisms found in the excrement of mammals and birds can thrive at temperatures around about 37° C. (100° F.), while other microorganisms can thrive at other temperatures. As another example, some microorganisms thrive in the hot mud bubblers of Yellowstone National Park or in various seamounts. See, e.g., Emerson, D., & Moyer, C. (2010, March), *Microbiology of Seamounts*, 23 Oceanography at 148-163, which is herein incorporated by reference in its entirety. In other embodiments, the trench 106 can be arranged to vary the temperature across the length of the outer tube 103. For example, one section of the outer tube 103 can have a temperature that eliminates pathogens harmful to humans, while another section of the outer tube 103 can have a temperature that optimizes system efficiency in cold environments (e.g., subarctic environments).

FIG. 1C is a cross-sectional diagram of the outer tube 103. In the illustrated embodiment, the outer tube 103 includes a circular (or rounded) wall 120 defining an opening 122 with a first diameter $d_1$. In one embodiment, the circular wall 120 is generally rigid and is formed, for example, from a hard plastic. In another embodiment, the circular wall 120 is flexible and is formed, for example, from a flexible plastic. In the latter embodiment, the circular wall 120 can be configured such that it does not substantially expand (e.g., inflate) under regular operating conditions.

The outer tube 103 further includes deformable tubes 125 (identified individually as a first deformable tube 125a and a second deformable tube 125b) and at least one of the gas collection conduits 114 (e.g., tubes having molecular sieves, slits, and/or pores; not shown). The deformable tubes 125 extend through the outer tube 103 and individually include a flexible wall 126 and an interior 128 defined in part by the flexible wall 126. In one embodiment, the flexible wall 126 is formed from a flexible polymer, such as polyolefin. In operation, the flexible wall 126 can expand and contract to locally change the volume of the interior 128. In general, the flexible wall 126 expands when liquid fills the interior 128. As described in greater detail below, when the liquid applies pressure on the flexible wall 126, it can contract a neighboring (less-pressurized) deformable tube 125 to evacuate the liquid from this tube.

FIG. 1D is a cross-sectional diagram of one of the deformable tubes 125 (in a non-deformed state). The flexible wall 126 can have a second diameter $d_2$ that is smaller than the first diameter $d_1$ of the outer tube 103 (FIG. 1C). The second diameter $d_2$, however, is greater than at least one-half of the first diameter $d_1$ of the outer tube 103. Although shown as circular for purposes of illustration, the flexible wall 126 can have any of a variety of different shapes and/or sizes to provide for a desired deformation (and attendant expansion/contraction). For example, in one embodiment the flexible wall 126 can have an ovular shape.

The interior 128 of the deformable tube 125 includes a surface 129 at the flexible wall 126 and internal elements 130 attached to (or formed in) the surface 129. The internal elements 130 can include, for example, string elements 130a, flap elements 130b, ripple elements 130c, and/or tubule elements 130d. In operation, the internal elements 130 provide surface locations at which microorganisms can attach (i.e., in addition to the surface 129). In some embodiments, the internal elements 130 can provide additional or alternative functions. For example, the tubule elements 130d can be configured to stagnate water, transfer heat, and/or create different temperatures (e.g., thermal flywheels) in the digestion region 105 (FIG. 1A). In other embodiments, the surface 129 and/or the internal elements 130 include chemical and/or material coatings (not shown) that promote biofilm growth as well as microorganism attachment. For example, such coatings can contain trace materials.

FIGS. 2A-2C are isometric diagrams that show various stages in a method for manufacturing the deformable tubes 125 of the digester 102 from a thermoplastic material 240. Referring first to FIG. 2A, an extrusion molding process can form the material 240 to include the flexible wall 126 and the surface 129 (shown on the exterior of the material 240). In one embodiment, pressurized/vacuum cavities (i.e., in the mold tooling) can draw discrete portions of the material 240 away from the flexible wall 126. Rapid cooling of these portions can harden these discrete portions to define the tubule elements 130d. Referring to FIG. 2B, with the surface 129 facing outward, the method can further include forming the internal elements 130 on the surface 129 of the material 240. The internal elements 130 can be welded, thermally fused (e.g., via laser, resistance, and/or vibrational techniques), or otherwise adhered to the surface 129. In one embodiment, tabs, strips, stings, etc., can be positioned and adhered to form the internal elements 130. In another embodiment, the surface 129 can be scored, patterned, and/or otherwise mechanically, chemically, and/or electrically treated. Referring to FIG. 2C, the surface 129 can then be rolled inwardly (as designated by arrows 242) to position the internal elements 130 within the interior 128 of the flexible wall 126.

Figure 3:
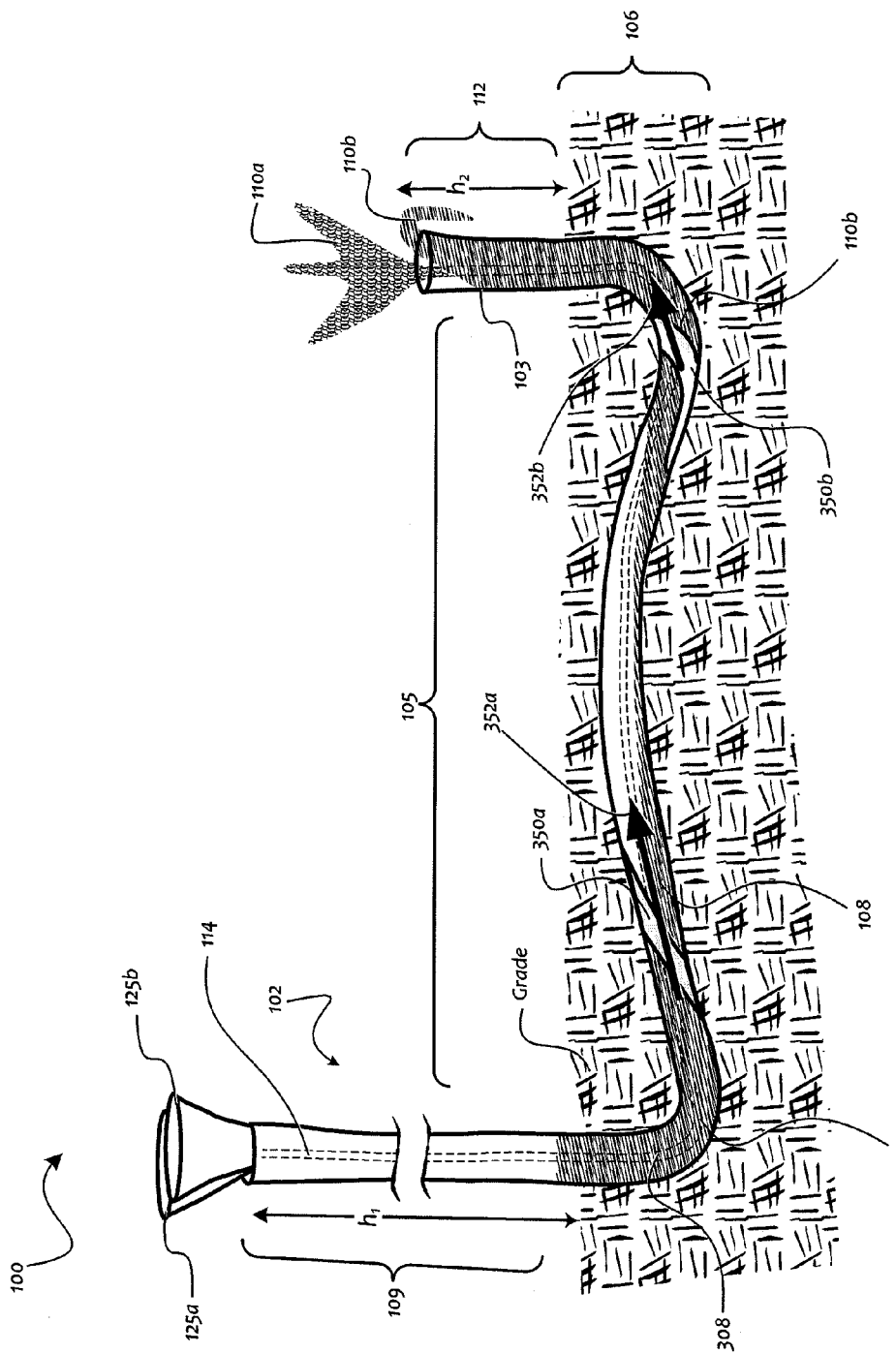
FIG. 3 is a diagram showing example operation of the system of FIGS. 1A-1D in accordance with an embodiment of the present technology.

FIG. 3 is a diagram showing example operation of the system 100. In particular, FIG. 3 shows the digester 102 of FIG. 1 after it receives replenishment waste liquid 308 ("replenishment liquid 308"). For purposes of illustration, the liquid waste 108 is described as residing (or flowing) in the first deformable tube 125a, the replenishment liquid 308 is described as residing (or flowing) in the second deformable tube 125b, and the liquid byproducts 110b are described as residing (or flowing) in the first deformable tube 125a. A person of ordinary skill in the art will recognize, however, that the deformable tubes 125 can be filled with liquids in a different sequence.

Prior to receiving the replenishment liquid 308, the liquid waste 108 closes or substantially closes the second deformable tube 125b toward the input region 109 of the digester 102 (represented by a first seal 350a). Similarly, the liquid byproducts 110b close the second deformable tube 125b toward the output region 112 (represented by a second seal 350b). As described above, liquid can expand one of the deformable tubes 125 while closing the other.

When the replenishment liquid 308 enters the second deformable tube 125b, it applies a pressure to move the liquid waste 108 in the first deformable tube 125a toward the output region 112. This pressure can be based at least in part on the volume, mass, and height (i.e., the height above $h_2$) of the replenishment liquid 308 in the second deformable tube 125b. As the force increases, the liquid waste 108 begins to flow toward the liquid byproducts 110b (as represented by a first arrow 352a) in the first deformable tube 125a. The liquid waste 108 can then apply a pressure on the first deformable tube 125a at the output region 112. This in turn delivers a volume of the liquid byproducts 110b toward the output region 112 (as represented by a second arrow 352b). The liquid waste 108 can also seed further anaerobic processes and in turn generate more byproducts.

In addition, the peristaltic-like motion of the deformable tubes 125 evacuates gases. In particular, the compression of the deformable tubes 125 causes air and the gas byproducts 110a to evacuate through the gas collection conduits 114. In one aspect of this embodiment, the evacuation of air maintains the anaerobic environment which in turn conserves food sources that would otherwise rot outside this environment (e.g., animal excrement, plant wastes, and other substances). In another aspect of this embodiment, the evacuation of the gas byproducts 110a seeds further digestion. In one embodiment, the relatively higher solubility of carbon dioxide in water can facilitate methane collection. For example, elevated amounts of carbon dioxide can create a buoyant force that enhances methane separation.

After an appropriate amount of dwell time, additional replenishment waste liquid (not shown) can be supplied to the first deformable tube 125a to displace the replenishment liquid 308 in a similar manner as that described above. In one embodiment, the dwell time of the liquid waste 108 (i.e., before replenishment) is relatively short. For example, the replenishment liquid 308 can be provided within seconds, minutes, or hours of receiving the liquid waste 108. In another embodiment, however, the dwell time can be longer (e.g., days, weeks, or months). In general, the dwell time can be based on factors such as the operating conditions (e.g., temperature, liquid pH, etc.), the demand for the byproducts 110, and/or the type of microorganisms within the digester 102. For example, certain anaerobic digestive processes can require longer dwell times than others.

In some embodiments, the digester 102 can be configured to utilize certain additives that promote microorganism digestive processes. In one embodiment, for example, termites can be added to the digestion region 105 and wood can be a solid phase components of the liquid waste 108. The termites can facilitate breakdown of the wood into components that are more readily digestible by the microorganisms. These components can accelerate the overall rate of recovery of the byproducts 110. For example, termites can enzymically make the components required for bacteria to produce methane. In addition, termites can provide heat stock for promoting microorganisms. In certain embodiments, termites can be selected based on the type of food source they require. For example, some termites are faster digesters than others for certain types of wood, grass, forest slash, etc.

In various embodiments, the digester 102 can be particularly suited for deployment to remote communities and geographical regions. In particular, the digester 102 can be relatively easy to assemble and can include lightweight and inexpensive components. As such, an organization, government, or the like can readily ship a container that contains the digester components and assembly instructions. In one embodiment, the material of the outer tube 103 and/or the deformable tubes 125 can deflate, yet still have sufficient thickness to resist plastic deformation. For example, these materials can include polymeric materials, such as polyolefin, that can lay flat and be rolled up for compact shipping.

Accordingly, in these and other embodiments, the digester 102 can economically provide energy, potable water, and/or food sources. In addition, the digester 102 can provide other advantages. In one embodiment, liquid (acidic) byproducts 110b can be output to an electrolyzer to create hydrogen. This hydrogen can be used separately or in combination with gas byproducts 110a (e.g., methane) for cooking or operation of an engine or fuel cell. In another embodiment, liquid byproducts can include water that is recycled into the system 100 for mixing and de-aeration and/or heat transfer (e.g., as part of heat-transfer elements 115; FIG. 1B). In yet another embodiment, liquid byproducts can include carbon dioxide-rich water to stimulate growth of garden crops, duckweed, and/or algae. This can also enable job development and local food production of garden vegetables and high-value protein. For example, fish, such as tilapia, can feed on fluid byproducts that include duckweed and/or algae.

The foregoing description of embodiments of the invention are not intended to be exhaustive or to limit the invention to the precise embodiments disclosed. While specific embodiments of, and examples for, the invention are described herein for illustrative purposes, various equivalent modifications are possible within the scope of the invention, as those of ordinary skill in the relevant art will recognize. For example, although certain functions may be described in the disclosure in a particular order, in alternate embodiments these functions can be performed in a different order or substantially concurrently, without departing from the spirit or scope of the disclosure. In addition, the teachings of the disclosure can be applied to other systems, not only the representative card vending systems described herein. Further, various aspects of the invention described herein can be combined to provide yet other embodiments.

All of the references cited herein are incorporated in their entireties by reference. Accordingly, aspects of the invention can be modified, if necessary or desirable, to employ the systems, functions, and concepts of the cited references to provide yet further embodiments of the invention. These and other changes can be made to the invention in light of the above-detailed description. In general, the terms used in the following claims should not be construed to limit the invention to the specific embodiments disclosed in the specification, unless the above-detailed description explicitly defines such terms. Accordingly, the actual scope of the invention encompasses the disclosed embodiments and all equivalent ways of practicing or implementing the invention under the claims.

Unless the context clearly requires otherwise, throughout the description and the claims, the words "comprise," "comprising," and the like are to be construed in an inclusive sense as opposed to an exclusive or exhaustive sense, that is to say, in the sense of "including, but not limited to." Words using the singular or plural number also include the plural or singular number respectively. Additionally, the words "herein," "above," "below," and words of similar import, when used in this application, shall refer to this application as a whole and not to any particular portions of this application. When the claims use the word "or" in reference to a list of two or more items, that word covers all of the following interpretations of the word: any of the items in the list, all of the items in the list, and any combination of the items in the list.

From the foregoing, it will be appreciated that specific embodiments of the invention have been described herein for purposes of illustration, but that various modifications may be made without deviating from the spirit and scope of the various embodiments of the invention. Further, while various advantages associated with certain embodiments of the invention have been described above in the context of those embodiments, other embodiments may also exhibit such advantages, and not all embodiments need necessarily exhibit such advantages to fall within the scope of the invention. Accordingly, the invention is not limited, except as by the appended claims.

I claim:

1. A renewable energy system, comprising a digester assembly that includes:
   first and second deformable tubes each having an outer diameter and including an input region, an output region, and a digestion region therebetween, wherein the digestion region is configured to receive the liquid waste via the input region and to anaerobically digest liquid waste with microorganisms to supply renewable byproducts, and
   an outer tube configured to be installed below grade and to substantially contain the first and second deformable tubes, wherein the outer tube has an inner diameter that is less than the sum of the outer diameters of the first and second deformable tubes, and wherein the inner diameter of the outer tube is the selected such that when the liquid waste is received into the second deformable tube via the corresponding input region, fluid pressure in the second deformable tube expands the second deformable tube and compresses the first deformable tube between the second deformable tube and the outer tube to force liquid in the digestion region of the first deformable tube downstream toward the corresponding output region.

2. The system of claim 1 wherein:
the first input region is configured to extend above grade by at least a first height; and
the output region is configured to extend above grade by at least a second height that is less than the first height.

3. The system of claim 1 wherein the liquid waste includes at least one of animal waste, plant waste, and/or soil waste.

4. The system of claim 1 wherein the byproducts include at least one of methane, hydrogen, and/or carbon dioxide.

5. The system of claim 1 wherein the byproducts include carbon dioxide-rich water.

6. The system of claim 1 wherein the digestion region is positioned within a trench that contains at least one of an insulating material, a heat-transfer element, and/or drainage.

7. The system of claim 1, wherein:
the byproducts include liquid byproducts; and
the first and second deformable tubes are further configured to output at least a portion of the liquid byproducts.

8. The system of claim 1, wherein:
the byproducts include gas byproducts; and
the first and second deformable tubes are further configured to evacuate the gas byproducts.

9. The system of claim 1 wherein the first and second deformable tubes are further configured to exhaust air to promote the anaerobic digestion of the liquid waste.

10. The system of claim of 1 wherein each of the first and second deformable tubes include:
a flexible wall defining an interior surface; and
internal elements operably arranged with the interior surface, wherein the internal elements are configured to provide surface locations at which microorganisms can attach for anaerobic digestion within the tube.

11. The system of claim 10 wherein the internal elements include at least one of string elements, flap elements, ripple elements, and/or tubule elements.

12. The system of claim 10 wherein at least one of the interior surface and/or the internal elements includes a surface coating that is configured to promote biofilm growth and/or microorganism attachment.

13. The system of claim 10, further comprising at least one gas collection conduit substantially contained within the first deformable tube and/or the outer tube, wherein the at least one gas collection conduit includes a gas permeable wall defining an interior region configured to receive gaseous products through the permeable wall.

* * * * *

UNITED STATES PATENT AND TRADEMARK OFFICE
CERTIFICATE OF CORRECTION

PATENT NO. : 9,127,244 B2  
APPLICATION NO. : 13/828549  
DATED : September 8, 2015  
INVENTOR(S) : Roy Edward McAlister Page 1 of 1

It is certified that error appears in the above-identified patent and that said Letters Patent is hereby corrected as shown below:

Title Page, item (56)

On page 3, in column 1, under "Other Publications", line 29, delete "PCT/USUS10/24497," and insert -- PCT/US10/24497, --, therefor.

On page 3, in column 1, under "Other Publications", line 32, delete "PCT/USUS10/24496," and insert -- PCT/US10/24496, --, therefor.

On page 3, in column 1, under "Other Publications", line 35, delete "PCT/USUS10/24498," and insert -- PCT/US10/24498, --, therefor.

In the Claims

In column 6, line 60, in claim 1, after "is" delete "the".

In column 8, line 4, in claim 10, delete "of claim of" and insert -- of claim --, therefor.

Signed and Sealed this  
Nineteenth Day of April, 2016

Michelle K. Lee  
*Director of the United States Patent and Trademark Office*